(12) United States Patent
Kristjansson

(10) Patent No.: US 9,757,055 B2
(45) Date of Patent: Sep. 12, 2017

(54) METHOD FOR ACCURATE ASSESSMENT AND GRADED TRAINING OF SENSORIMOTOR FUNCTIONS

(75) Inventor: Eythor Kristjansson, Reykjavik (IS)

(73) Assignee: NECKCARE LLC., Fort Myers, FL (US)

( * ) Notice: Subject to any disclaimer, the term of this patent is extended or adjusted under 35 U.S.C. 154(b) by 0 days.

(21) Appl. No.: 13/382,422

(22) PCT Filed: Jul. 7, 2010

(86) PCT No.: PCT/IS2010/000010
§ 371 (c)(1),
(2), (4) Date: Feb. 13, 2012

(87) PCT Pub. No.: WO2011/004403
PCT Pub. Date: Jan. 13, 2011

(65) Prior Publication Data
US 2012/0133655 A1 May 31, 2012

(30) Foreign Application Priority Data
Jul. 7, 2009 (IS) .............................. 8835

(51) Int. Cl.
*G06T 15/00* (2011.01)
*G06F 15/00* (2006.01)
*A61B 5/11* (2006.01)

(52) U.S. Cl.
CPC .......... *A61B 5/1122* (2013.01); *A61B 5/1124* (2013.01)

(58) Field of Classification Search
None
See application file for complete search history.

(56) References Cited

U.S. PATENT DOCUMENTS

| | | | |
|---|---|---|---|
| 5,954,974 A | 9/1999 | Broer | |
| 2008/0266250 A1 | 10/2008 | Jacob | |
| 2010/0016754 A1* | 1/2010 | Whillock et al. | 600/558 |

FOREIGN PATENT DOCUMENTS

| | | |
|---|---|---|
| WO | 911514 A1 | 10/1991 |
| WO | 0176478 A1 | 10/2001 |
| WO | 2004043257 A1 | 5/2004 |

OTHER PUBLICATIONS

Oddsdottir, "Cervical induced balance disturbances after motor vehicle collisions; The efficacy of two successive physical treatment approaches," (Thesis for a Master of Science degree, University of Iceland, Jun. 2006).*
Edelsbrunner et al. "Arrangements of curves in the plane-topology, combinatorics, and algorithms" (Theoretical Computer Science, vol. 2 (1992) pp. 319-336).*
Viviani et al. "Minimum-Jerk, Two-Thirds Power Law, and lsochrony: Converging Approaches to Movement Planning" (Journal of Experimental Psychology, vol. 21 (1995) pp. 32-53).*
Kristjansson et al. "Sensorimotor Function and Dizziness in Neck Pain: Implications for Assessment and Management" (Journal of Orthopaedic and Sports Physical Therapy, vol. 39 (2009) pp. 364-377).*
Townley Slinger, et al, "Brain-Part 1 1906, Original Articles and Clinical Cases" From the Neurological Research Department, National Hospital, Queen Square, Loudon and the Psychological Laboratory, Cambridge, pp. 2-28.
Eythor Kristjansson, "Cervicocephalic kinaesthesia: reliabilty of a new test approach", Pysiotherapy Research International, 6(4) 224-235, 2001, pp. 224-235.
Hannu Heikkila, "Cervicocephalic Kinesthetic Sensibility in Patients With Whiplash Injury", Sacnd J Rehab Med 28: 133-138, 1996, pp. 134-138.
Eythor Kristjansson, "A New Clinical Test for Cervicocephalic Kinesthetic Sensibility: The Fly", Arch Phys Med Rehabil vol. 85, Mar. 2004, pp. 490-495.
Janice K. Loudon, "Ability to Reproduce Head Position After Whiplash Injury", Ovid: Loudon: Spine, vol. 22(8), Apr. 15, 1997, pp. 865-868.
Michel Revel, "Cervicocephalic Kinesthetic Sensibility in Patients with Cervical Pain", Arch Phys Med Rehabil vol. 72, Apr. 1991, pp. 288-291.
George D. Rix, "Cervicocephalic Kinesthetic Sensibility in Patients With Chronic, Nontraumatic Cervical Spine Pain", Arch Phys Med Rehabil vol. 82, Jul. 2001, pp. 911-919.
International Search Report PCT/IS2010/000010; Dated Nov. 8, 2010.

* cited by examiner

*Primary Examiner* — Anna Skibinsky
(74) *Attorney, Agent, or Firm* — Cantor Colburn LLP

(57) ABSTRACT

The invention relates, to the field of motion tracking and sensorimotor assessment and training, by providing a method, system and software for tracking of a target by moving the head and neck or other body part in two or three-dimensional space. In particular the invention teaches a method to create incremental difficult classes of unpredictable movement patterns according to specific criteria. The created movement patterns can be used to accurately grade the deficits of movement control and other sensorimotor deficits of the head/neck and consequently a treatment can be prescribed which starts at each patient's impairment level by using the same method. The invention provides also a reliable and valid method to detect fraudulent neck compensation claims from genuine deficits by said assessment of sensorimotor function.

22 Claims, 3 Drawing Sheets

METHOD FOR ACCURATE ASSESSMENT AND GRADED TRAINING OF SENSORIMOTOR FUNCTIONS

FIELD OF THE INVENTION

The present invention relates, in general, to the field of body sensorimotor motion assessment and training, and in particular to a method, which can create an almost infinite number of incremental difficult classes of unpredictable movement patterns according to specific criteria.

TECHNICAL BACKGROUND AND PRIOR ART

Persistent neck pain of greater than six months duration is a frequent occurrence in both men and women and patients with neck pain are the second biggest group (after patients with low back pain) attending physical therapy and chiropractic clinics for relief of their symptoms. Further, research shows that about one third of patients diagnosed with whiplash associated disorders, (a variety of clinical manifestations due to bony or soft tissue neck injuries following an acceleration-deceleration energy transfer sustained from a motor vehicle accident), only gain short-term relief by conventional musculoskeletal approaches, which by definition are an ineffective treatment. Preventing a portion of patients with neck pain to enter the chronic phase of their condition imposes a great challenge for clinicians.

Non-invasive methods have been developed to quantify abnormal motions of the cervical spine segments using biomechanical parameters. Patent application W0 91/15148 discloses a method that uses instantaneous axis of rotation (IAR) of normal and abnormal Range of Motion. Measurement of the IAR detects kinematic joint function but not sensorimotor function. The same applies to the method disclosed in U.S. Pat. No. 5,954,674, where each patient is trained to move his/her head in a predetermined manner in predetermined planes of motion at a predetermined velocity. While the patient moves the joint in the aforementioned predetermined single plane of motion, biomechanical data is gathered pertaining to the instantaneous helical axis of rotation of the cervical spine segments.

Patent application W0 2004/043257 describes a device for the diagnosis and/or therapy of functional disorders of the cervical spine. The patient is required to follow an optical signal with the head by a tracking system which moves along a predetermined horizontal or vertical line/path at a predetermined speed in a recurring way. The path is usually a straight line but with a specific vertical or horizontal displacement/deflection or amplitude. To make the movement path easier or more difficult the length of the movement line can be shortened or made longer and the speed at which the optical signals moves for a given path can be reduced or increased. W0 2004/043257 uses electromyography (EMG) signals from the muscles, especially m. semispinalis capitis, as an outcome measure.

The observed individuality in sensorimotor disturbances in patients with neck pain suggests that it may be important to develop specific rehabilitation programs for specific dysfunctions and to use objective and quantitative methods for evaluation of the effects of rehabilitation. The term "sensorimotor" incorporates all the afferent, efferent, and central integration and processing components involved in maintaining stability in the postural control system through intrinsic motor control properties. From a clinical orthopaedic perspective, the peripheral mechanoreceptors are the most important in functional (muscular-neural) joint stability but in the cervical region they are also important for postural stability, head-neck and eye movement control.

Consequently, conventional musculoskeletal approaches may be sufficient only for patients with neck pain and minimal sensorimotor disturbances. Clinical experience and research indicates that in cases of significant sensorimotor disturbances, this might be an important factor in the maintenance, recurrence, or progression of various symptoms in patients with neck pain. In these cases more specific and novel treatment methods are needed which progressively address neck position and movement sense as well as cervicogenic oculomotor disturbances, postural stability, and cervicogenic dizziness.

Since they were introduced in 1906 by Slinger and Horsley (Slinger (1906)), simple target-matching tasks have been widely used clinically to measure accuracy of movement. The neuromuscular mechanism controlling the head on the body has been tested either by relocation of the natural head posture (NHP) (Revel (1991), Heikkilä (1996), Rix (2001)) or relocation of a set point in range. (Loudon (1997)) These traditional cervicocephalic kinesthetic tests are limited because they measure only one aspect of proprioceptive function: position sense. An important function of the proprioceptive system in neuromuscular control is to correct movement on a moment-to-moment basis. This is especially the case when non-learned complex movements are performed.

In a prior study (Kristjansson (2001)) subjects were required to trace a discreet figure of 8—movement by repeated movements of their head. Each time a cross-over in the figure of 8 was made, the subjects were asked to move their nose through the starting natural head posture (NHP) as accurately as possible. This test was too difficult for both asymptomatic and symptomatic subjects to be clinically useful.

A "laser beam method" has been used by some therapists to track predetermined patterns such as a figure of eight, ellipsoids, polygons and the like, placed in front of the patient (See patent application WO 01/76478). The motion patterns in the laser beam method are highly predictable and therefore do not challenge the proprioceptive system, which needs unpredictable movement patterns of incremental difficulty for accurate assessment and to enhance treatment progression. Furthermore, the outcome measures in the laser beam method are not readily available for clinical judgment of the patient's ability to trace the pattern accurately and smoothly and the most important variables (amplitude accuracy, directional accuracy and jerk index), are not used (as in the present invention) to monitor the status of each patient's sensorimotor movement control for objective assessment and to enhance graded progression in the treatment of said sensorimotor impairment.

Inventor's previously introduced clinical method measures the patient's ability to correct cervical spine movements on a moment-to moment basis, which is an important proprioceptive function for the regulation of movements, i.e. detection and correction of errors, when performing active movements, via feedback and reflex mechanisms. This method and system, called "the Fly" demonstrated impaired movement patterns in patients with a whiplash injury when compared to controls. (Kristjansson (2004)).

Different theories about motor control such as reflex, hierarchical and system theories underpin the design of this prior test. (Shumway (2001)). These theories suggest that the test movement needs to be slow, unpredictable and of short duration in order to challenge deficits in the cumulative input from the mechanoreceptors which give rise to neck proprioception. The slow speed ensures that over-stimulation of the neck mechanoreceptors and of the specialised mechanoreceptors in the vestibular system is avoided. A slow speed is also necessary for the subjects to be able to rely on feedback from the neck mechanoreceptors during movement. The movement path must be unpredictable and of short duration to avoid programming and learning effects. In addition, the system theories tell us that because the final goal of a movement takes priority over everything else during task performance, movement paths for the same task may differ each time the task is repeated. An unpredictable test path is therefore preferred.

In "the Fly" (Kristjansson (2004)), the patient sits in front of a computer with one or more sensor mounted on the head, which accurately measures the positions and movements of the head-neck in space. Two cursors are visible on the computer screen: one black indicating the movements of the head-neck sensor and the other blue, the target cursor derived from "the Fly" software program, which target cursor traces the path to be followed. At the very beginning of the test both cursors match each other in the middle of the screen. Then the blue target cursor starts to move. The patient is instructed to follow "the Fly" cursor, tracing slow movement patterns of short duration, with the black cursor, by moving the head-neck and thus the mounted sensor, as accurately as possible. The deviation or amplitude accuracy between the two cursors is continuously recorded during three randomly ordered test sequences.

It would however be appreciated to be able to more precisely grade the impairment level of an individual patient and use such a motion tracking method and system as a treatment method, starting at each individual's respective impairment level and going through progressively more difficult levels of training.

SUMMARY OF INVENTION

The present invention provides a method and a system used to accurately assess the deficits of movement control and other sensorimotor deficits of the head/neck region or the limbs. Consequently a treatment can be prescribed which starts at each patient's sensorimotor impairment level by using the same method. Furthermore, the invention provides a reliable and valid method to detect fraudulent neck compensation claims from genuine deficits by said assessment of sensorimotor function.

The solution provided by the present invention solves two related problems, the first being an assessment method and the second being an exercise method. Both solutions are provided as software programs implemented as a combination of software, computers, monitors and motion sensors, where generated movement patterns are imported from a Pattern Generation Program into two other new software programs. These software programs can be made available to the patients from a remote server over the Internet.

A primary object of the invention is to provide an improved method for assessment and training of a person's sensorimotor control deficits. The present invention improves the previously developed system by generating movement patterns with incremental difficulty levels. The method is realized through a new software program, which can generate almost infinite number of movement patterns according to specific criteria. The specific criteria are based upon predefined parameters which form the boundaries for each of the different classes of movement patterns generated. Many classes of movement patterns can thereby be generated and applied in accordance with the present invention.

In motor skill learning it is important that the level of task difficulty is adjustable to the individual patient's skill level to ensure that the exercise is neither too difficult nor to trivial to perform. This aspect has been highlighted in the challenge point framework theory. The optimal challenge point represents the degree of task difficulty needed for an individual of a specific skill level to optimize learning. By adjusting the task difficulty to the change in ability, the optimal challenge point is maintained. This is accomplished by moving on to the next difficulty level in the said incremental set of unpredictable movement patterns.

In a first aspect the invention provides a method for assessing sensorimotor function of a human subject which comprises
generating in a computer a pattern which comprises a trajectory path,
placing a movement sensor on the head or limb of said subject, which sensor is connected to said computer such that said computer can trace movements of said sensor, and output a tracing cursor on a display,
drawing said trajectory path on said display with a target cursor after the subject has been instructed to follow the target cursor by moving the tracing cursor,
measuring the correlation and/or deviation of said tracing cursor from said target cursor,
providing an assessment of sensorimotor function of said subject, based on the measured correlation and/or deviation in previous step,
wherein the method is characterised by in that said generated pattern is pre-classified in a class from a plurality of difficulty classes of patterns of incremental difficulty.

In a further aspect, a system is provided for assessing and training sensorimotor function of a human subject, the system comprising:
a computer installed with a computer program,
an output display connected to said computer,
a motion tracking sensor connected to said computer,
said computer program when run on the computer generates a pattern comprising a trajectory path that is traced on said display with a target cursor,
the program further outputs on the display a tracking cursor, which follows the motion of said motion sensor,
the program calculates a correlation and/or deviation between said target cursor trajectory and the trajectory of the tracking sensor, and outputs data indicative of the sensorimotor function of the subject,
the program is capable of generating a plurality of difficulty classes of patterns of incremental difficulty.

In yet a further aspect, the invention provides a computer software product for assessing and training sensorimotor function of a human subject, which when installed and run on a computer generates a pattern comprising a trajectory path that is traced on said display with a target cursor, the program further outputs on the display a tracking cursor, based on a signal received from a motion sensor connected to said computer, thus the tracking cursor follows the motion detected by said motion sensor,
the program calculates a correlation and/or deviation between said target cursor trajectory and the trajectory of the tracking sensor, and outputs data indicative of the sensorimotor function of the subject,
the program being capable of generating a plurality of difficulty classes of patterns of incremental difficulty, and selecting and/or suggesting a suitable difficulty level for a given subject based on said subject's assessment.

Parameters for creating incremental difficult classes of movement patterns and which form the boundaries between each class of movement patterns preferably include one or more of the following parameters, which are described and defined in more detail in the detailed description:

The number of curvatures (number of curves in the pattern path),

The acuity of a curvatures in a given movement class (how acute the curves are), The threshold defining where a curvature in a given movement pattern starts, The length of the trajectory of a pattern, The ratio between the curved versus the more straight parts of a given movement pattern, The speed of the target in the curved parts of a pattern on one hand and on the more straight parts in a pattern on the other hand, Adjustment of the movement sensitivity of the cursor/ crosshair guided by the sensor on the patient's head, i.e. the speed and reaction time of the cursor/crosshair, The speed of the target between two pixel point on the display device, and The size of the frame that the target is moving within on the display device.

In some embodiments two or more of the above mentioned parameters are used for creating the difficulty classes, such at least three parameters, or at least four or five of the above parameters, such as six or more of the parameters. In a preferred embodiment all of the above parameters are used in the method.

In embodiments where less than all of the above parameters are used, some of the parameters, those not used, may simply be permanently fixed so as to not have any variable effect on the created patterns and difficulty level classification.

After different classes of movement patterns have been generated once, new patterns can always be added within a movement class. New classes of movement patterns can always be generated by changing the values of the aforementioned parameters. A preselected pattern in whatever movement class can also be changed to make it easier or more difficult without changing other patterns at the same time.

It follows that when performing the method, a suitable pattern can be randomly selected by the computer in a defined difficulty class from a database of generated patterns, or a new pattern can be randomly calculated using one or more of the parameters mentioned herein and generated in situ, that is, prior to the instant performance. Such in situ generated pattern can subsequently be added to a database of patterns.

It will be appreciated that the invention allows the selection of a suitable difficulty class of patterns based on a prior assessment of a particular subject, i.e. a subject in need of sensorimotor assessment can be evaluated and based on the outcome, he/she can be enrolled in an exercise program, starting at a difficulty level selected based on the assessment.

The results of each run indicating sensorimotor function can be presented in various ways, in accordance with the invention. Preferably, the result provide more than one indicator and these can be combined in one grade. Preferably the outcome indicates one or more of the following: amplitude accuracy, directional accuracy, and jerk index, as defined herein.

In the most straight-forward embodiment of the invention, the patterns are two-dimensional and output on any type of conventional display. However, in a more advanced embodiment, the patterns can as well be calculated in three dimensions, where any type of three-dimensional output display can be used, such as 3-D stereogoggles.

Several variations are possible of the patterns in order to vary the difficulty and/or making the training more interesting and fun for the subject. In some embodiments, the pattern comprises a background on which the trajectory is drawn. The background can be a landscape picture o any photo or drawing or any abstract pattern background. In some embodiments, the background is moved relative to the trajectory pattern. The movement of the background can be in the same general direction as the target cursor or in a different direction, such as in a direction which is generally opposite to the direction of the target cursor. The cursors (target cursor and/or tracing cursor) can have any general shape. In a general embodiment, one or both cursors are simply shaped like a crosshair. However, the cursor can have e.g. the shape of an arrow, pointer, person, animal or the like shape.

In order to be more stimulating and entertaining, the patterns can be generated like a computer game, such as but not limited to designs where the tracing sensor is a beak of a bird tracing a target such as a fly, in such embodiments background patterns can be used, e.g. as dangerous landscapes, slalom runs, and the like, which may or may not be moving relative to the target, as described above. In certain embodiments, the target does not move along a continuous path but may appear and disappear at different time points, thus the subject can "chase" the target.

In some embodiments, a parameter is used to adjust the trajectory pattern to appear more in one particular quarter of the display, e.g. in the lower left quarter. This can be particularly useful in the training exercises, when the subject needs to train movements of the head and neck which involve bending the neck down to the left.

In other embodiments, the patterns can be adjusted so as to be more in a particular plane, which is referred to herein as "movement plane specific" patterns. Thus, the patterns in such embodiments can be more in e.g. sagittal, frontal or transverse planes, respectively, or more in two of such planes than the third one. In those embodiments it will be particularly useful to be able to provide and display three-dimensional trajectory patterns.

As will be evident from the detailed examples described herein, the invention is particularly suitable for evaluation of the sensorimotor function of the head and neck, such as after whiplash neck trauma or other injury or stress/work related conditions. However, the invention is equally applicable for sensorimotor assessment and training of other body parts and muscular areas, such the hand, wrist, elbow or arm, and also the foot or leg. This is readily accomplished by placing the sensor on a suitable location such as the hand, forearm, upper arm, foot, calf, knee or other suitable location depending on the body part or parts being assessed and trained. In one such embodiment, the method and system of the invention is used to assess tremors in the hands. Then, the movement sensor is in the form of a stylus and the subject holds the stylus in his hand and traces a target cursor displayed in this case on a touchpad drawing board. The embodiment can be suitably used to train subjects, e.g. subjects with diverse neurological disorders and elderly subjects with deteriorating sensorimotor function affecting fine movements of the hands e.g. when writing.

In useful embodiments, the method further comprises applying external stimuli and/or perturbations in any form to the subject during the assessment and/or exercise. Such external perturbations can involve vibration stimuli at various frequencies, in particular for the superficial neck muscles and/or for the superficial muscles at a remote body site. Such external perturbations may also involve unstable sitting or standing surfaces or external weights applied to subject's body.

The invention is useful for evaluation of whiplash associated disorders (WAD). Of persons that seek medical attention after traffic collisions for neck pain, about 20-40% remain symptomatic after six months and develop chronic whiplash associated disorders (WAD). Chronic WAD is difficult to treat and to accurately assess as usually no demonstrable path-anatomical signs can be detected that justify and accurately correlate with the disorder. Medical personnel therefore have to rely on patient's own experience. There is a substantiated concern that a proportion of those who claim compensation for whiplash injury are exaggerating or falsifying symptoms. This also negatively affects the majority of claimants with true symptoms, whose claims may be faced with doubts.

The present method is shown to statistically reliably differentiate between true responses of persons suffering from sensorimotor dysfunction, and persons who try to make up such symptoms. The true responders show a better consistency between tests and expected difference between different difficulty classes, while test subjects who were instructed to feign symptoms do not.

The method and system for measuring a person's ability to follow generated incremental difficult movement patterns is provided by the software to accurately assess the deficits of movement control and other sensorimotor deficits of the head/neck region or the limbs. The method provides three complementary outcome measures, Amplitude Accuracy, Directional Accuracy and Jerk Index. The amplitude accuracy represents the deviation between a target and a cursor (the sensor) placed on the patient's body, which is continuously measured between each pixel point on a display device and converted into millimeters. The directional accuracy represents "time on target", "undershoots" (time behind target) versus "overshoots" (time ahead og target), each being indicated as the percent of the total time used to perform a trial for a given movement pattern. The Jerk Index represents a measurement of the smoothness of movement of each individual performance for each movement pattern indicated by a quantitative index from 0-10 or other numerical quantification.

The method and system for improving co-ordination of cervical spine movements is provided by a program containing several clusters (banks) of patterns for each class/grade of incremental difficult movement patterns. The difficulty of an exercise trial within each cluster (bank) of movement patterns is regulated by selecting one or more of the following options: 1) speed of the target cursor on the straight parts of a pattern's trajectory, (several speeds of the target cursor can be chosen); 2) size of the pattern trajectory can be diminished or enlarged (several sizes of the pattern trajectory can be chosen); 3 target cursor size can be diminished or enlarged (several sizes can be chosen); 4) direction of the target cursor can be changed to point in different directions (several directions can be chosen).

In an embodiment of the present invention feedback is given by the exercise program during and after an exercise trial. The feedback is can be in the form of results of performance where the patient is provided with constant feedback during performance of the exercise trial. The display of the tracing cursor from the sensor mounted on the patient can be changed depending on the distance of the cursor is from the target cursor. This feedback indicates the directional accuracy of the cervical spine movements. A second type of feedback is results of outcome on completion of the test shown in two ways:

1) By a graphical display, such as a column, pies or by any other display features, indicating the percent age of a) the time on target, b) the time behind target or undershoots, and c) the time ahead of target or overshoots. The feedback can be displayed within the same column by e.g. different patterns of colours or in separated columns.
2) By a graphical display of the trajectory of the target cursor pattern and the pattern traced by the patient after the exercise trial is finished. This feedback visually expresses the patient's amplitude accuracy. The display can be made by colour difference or shape of the trajectory of the target cursor pattern indicating the difference between the path traced by the target cursor the pattern traced by the patient with the tracing cursor.

In an embodiment of the present invention exercises are repeated, at regular intervals, over a period of time such as one or two weeks. Daily or regular exercises at regular intervals, for a predetermined time such as 1-60 minutes, or 5-45 minutes, or 20-30 minutes or, 10-15 minutes of training are performed by the patient and then a reassessment is performed. The reassessment will decide whether the patient can start on a more difficult stage in the exercise program.

DETAILED DESCRIPTION

Figure 1:
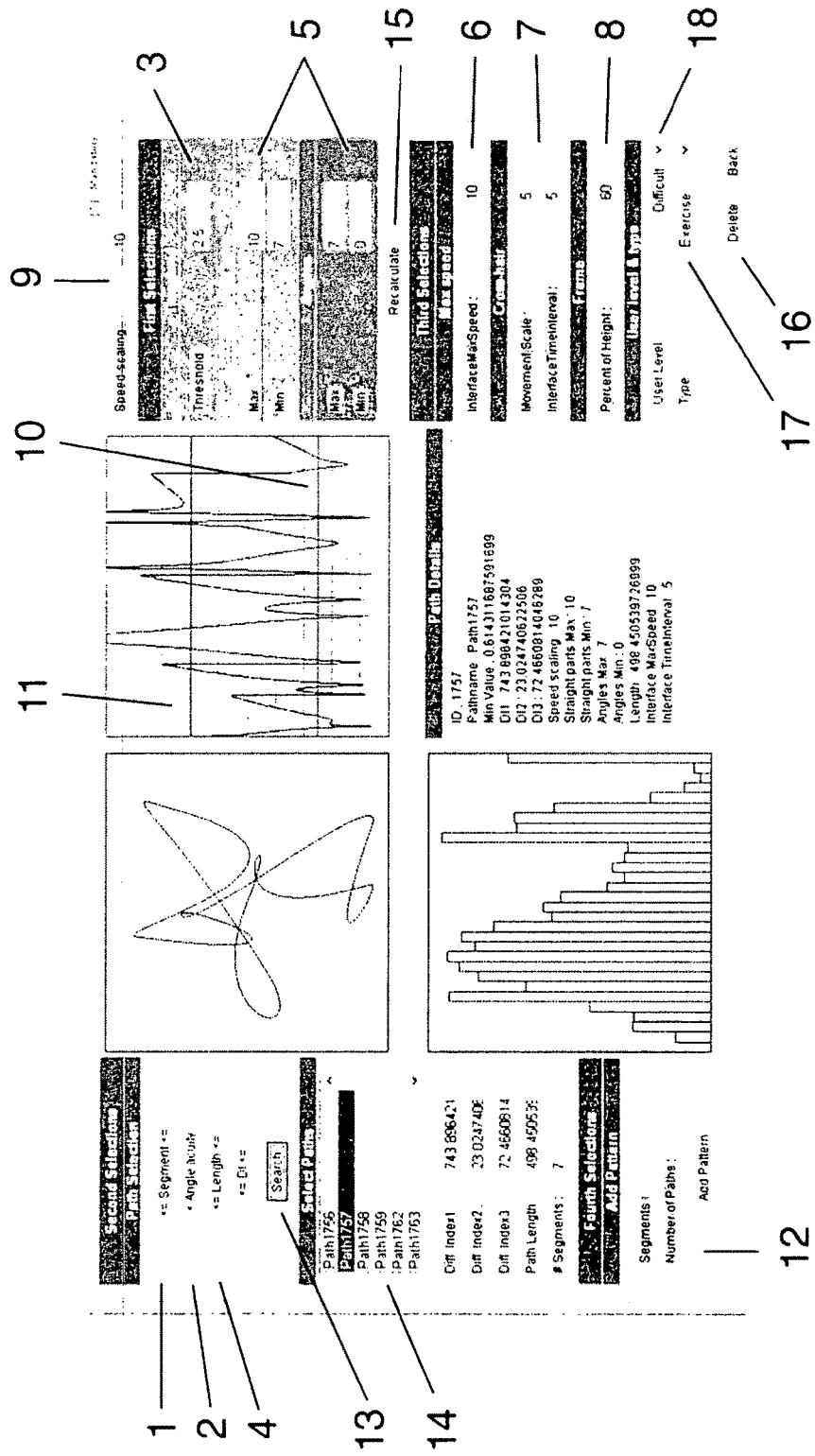
FIG. 1 is a screen shot of the menu in a Pattern Generation Program according to the invention.

The method of the present invention can suitably be performed at any location such at patient's home or local care facility. The subject will need obtain the movement sensor device and a computer. In one embodiment, the system is operated over a network, such the subject logs in through login access to the user interface of the software system. In such system, the patterns can suitably be stored and/or generated in a central computer and a suitable pattern forwarded to the user computer. The user computer is connected to the movement sensor such that the computer receives data representing the sensor movements during use. The correlation/deviation can be calculated with a program routine either in the user computer or preferably in the central computer. The central computer preferably collects some or all measurement data, making it possible to improve the comparison based on feedback and ongoing collection of historical data.

In an embodiment of the invention, the generated movement patterns are imported from a Pattern Generation Program into two other new software programs, one assessment program and another exercise program, which can be made available to the patients from a remote server over the Internet.

The two software programs are the following:
1. The Fly Assessment Software Program: This program measures a person's ability to follow the generated incremental difficult movement patterns by three complementary outcome measures:

Amplitude Accuracy: The deviation between a target (the Fly) and a cursor (sensor) placed on the patient's body is continuously measured between each pixel point on a display device and converted into millimeters.

Directional Accuracy: Time On Target, Undershoots versus Overshoots are each indicated as the percent of the total time used to perform a trial for a given movement pattern.

Jerk Index: Measures the smoothness of movement for each movement pattern indicated by a numerical index, e.g. from 0-10.

2. The Fly Exercise Program: Is a new computer generated exercise program designed to improve co-ordination of cervical spine movements. The program contains several banks for each class/grade of incremental difficult movement patterns. One or more of the following options can be chosen to make an exercise trial easier or more difficult for each pattern and/or bank respectively:

The speed of the target cursor on the straight parts of a pattern's trajectory, several speeds of the target cursor can be chosen;

The size of the pattern trajectory can be diminished or enlarged, several sizes of the pattern trajectory can be chosen;

The target cursor size can be diminished or enlarged; several sizes can be chosen The direction of the target cursor can be changed to point in different directions; several directions can be chosen Feedback During and after an Exercise Trial is an Essential Part of the Fly Exercise Program The following feedback is given:
1. Results of Performance: The patient is given constant feedback while performing the exercise trial. The tracing cursor from the sensor mounted on the patient changes color according to how close or how far the cursor is in relation to the target cursor. When the tracing cursor and the target cursor are in close approximation the tracing cursor is green. When the tracing cursor is behind or ahead of the target cursor, the tracing cursor is red and yellow respectively. This feedback indicates the directional accuracy of the cervical spine movements.
2. Results of Outcome: The results of outcome on completion of the test can be shown in the following two ways for the patient, as an example.

Firstly: By displaying a column, which indicates in percent a) the time on target, indicated by the green color in the middle of the column b) the time behind target or undershoots, indicated by the yellow color in the lower end of the column and c) the time ahead of target or overshoots, indicated by the red color in the upper part of the column.

Secondly: The trajectory of the target cursor pattern and the pattern traced by the patient is displayed graphically after the exercise trial is finished to visually express the patient's amplitude accuracy. The blue color represents the path traced by the target cursor and the green color represents the pattern traced by the patient with the tracing cursor.

After one or two weeks with daily or regular exercises at regular intervals, generally 10-15 minutes of training, reassessment is performed, which will decide whether the patient can start on a more difficult stage in the exercise program.

Thus, the present invention comprises both a new assessment and a treatment method to objectively measure and treat deficit sensorimotor control of cervical spine movements. This is accomplished by means of creating incremental difficult movement patterns according to pre-defined parameters (criteria). By this means the rehabilitation potential of a person's sensorimotor functions that depend on the sensory and motor function of the neck is increased.

Additional advantages and features of the invention are further defined in the depending claims as well as in the following more detailed description of preferred embodiments of the present invention.

FIG. 1 is a screen shot of the menu in the Pattern Generation Program It displays graphs, parameters and its respective data on the screen. Four square boxes are provided in the middle of the menu to view the generated pattern(s) in different forms after a pattern has been generated.

The top center-left box figure shows a particular pattern's trace.

The top center-right box graph shows a line graph of a pattern's trajectory speed—how the speed varies in a pattern from the start (left) to the end (right). The upper most part of the graph shows the more straight parts of a pattern trajectory with faster speeds while the lower part of the graph shows the more curved (angular) parts of a pattern trajectory with slower speeds.

The bottom center-left box shows a bar graph of a pattern's trajectory—how much time is relatively spend in different speed sections of a pattern, starting on the bottom left side (0%) and proceeding to the bottom right end (100%). This graph is mainly for enhancing visual understanding of the line graph (the top right box).

The bottom center right box lists the data of a pattern's trajectory (path) in more detail.

The pre-defined parameters or criteria for generating incremental different classes of movement patterns are divided into four main groups or selections: First Selections and Third Selections on the far right hand side in the menu and Second Selections and Fourth Selections on the far left hand side in the menu.

DETAILED DESCRIPTION OF A PREFERRED EMBODIMENT

A more complete understanding of the above-mentioned and other features and advantages of the present invention will be clear from the following, detailed description of preferred embodiments and definition of terms, where reference being made to the accompanying numbers in FIG. 1, wherein:
1. The number of curvatures or segments decide how often direction changes are implemented in each class of movement patterns.
2. The value in "Angle acuity" or the acuity of a curvature decides how acute/wide the curvatures in each class of movement patterns are. The lower the value the more acute the angles (curvature) and hence more difficult. The acuity of a curve determines the speed of the target in the curve according to the ⅔ Power Law which is programmed in the Software. In the original formulation of the ⅔ Power Law, the angular velocity and the curvature are related. The angular velocity is the quotient of the instantaneous velocity and the radius of curvature, and the curvature is the inverse of the radius of curvature. Basically the two-thirds power law states that the instantaneous velocity is lower in the more curved parts than in less curved parts of the trajectory.
3. The value of the threshold defines where a curvature in a given movement pattern starts. This is therefore a cut-off value. In this particular instance the value of the threshold is set at 2.5, meaning that fewer pixel points are calculated in the formula compared to when the threshold is set at a higher value. The ⅔ Power Law along with the value for the threshold (3) decides the value in Difficulty Index 1 (DI1). The higher the DI1, the more difficult the movement pattern.
4. The length limits of the trajectories in each class of movement patterns also decides the difficulty. The longer the trajectory, the more difficult the movement pattern. This option is also related to the number of segments (curvatures) in a said movement class as the numbers of curves in a given pattern are dependent on longer trajectories.
5. The values in the "Straight parts" versus "Angles" decide the ratio between the more straight parts versus curved parts of a given movement pattern. The value for Difficulty Index 2 (DI2) represents the straight parts or upper limits in a given pattern trajectory or line graph, respectively. Difficulty Index 3 (DI3) represents the curved parts or lower limits in a given pattern trajectory or line graph, respectively. DI2: This is the percentage of total points which have speed between "Straight parts"–"Max" and ""Straight parts"–"Min" i.e. DI2=100*(Number of points between these limits)/Total Points. DI3: This is the percentage of total points which have speed between ""Angles"–"Max" and "Angles"–Min".i.e. DI3=100*(Number of points between these limits)/Total Points.
6. "InterfaceMaxSpeed" in the Max speed option controls the speed on the straight parts in the pattern (upper limits). By choosing the same value as in Threshold (2) the speed in the straight parts (upper limits) becomes unchanged. By choosing a higher value for max speed in this option, the speed on the straight parts becomes faster.
7. The cross-hair option refers to the two cursors on the screen. A) This is a cross-hair representing the tracking cursor, relating to the sensor (tracker) on the patient's head. B) This is a cross-hair representing the target cursor.
7A) "Movement scale" is used to attenuate or multiply the "cross-hair movement" derived from the sensor, adjusting the movement sensitivity of the sensor/tracker. The higher this value the less movement is required by the sensor (tracker) to move the tracing cursor the same distance on the screen. A higher value here indicates wider angle and the reach of the cross-hair increases—and the patient moves in a bigger space on the screen. Then a lesser effort will be required by a patient to move when high movement scale value is specified. Therefore, it is easier for the patient to follow the target cursor on the screen derived from the software program. The converse is true when lower value is chosen for "Movement scale" as the angle becomes narrower and the reach of the cross-hair on the screen diminishes. An example: If movement scale value is set to 10 then every movement of the sensor is increased by 10 on screen which accelerates cross-hair movement on screen. Movement on screen is represented in pixels so every 1 pixel of movement by patient (cross-hair) is actually 11 pixels movement (1+10).
7B) TimeInterval decides the speed of the target crosshair between two pixel points on the display device. This cross-hair is derived from the software program (in the form of a Fly in this instance). By choosing a higher interval the velocity of the Fly becomes slower. TimeInterval is at the start tuned on a value and controls a "timer" which draws the Fly (timer interval). This "timer" ticks and draws "the Fly" by producing "SmoothSpeed( )" function. Each time the Fly is drawn its speed is compared with "maxSpeed"—if the Fly speed is below "maxSpeed" then the "timer.interval" is extended by multiplying the original set value with max speed/speed. On the other hand if the speed extends max speed then "timer interval" will be set at the original value in "TimeInterval".
8. Percent of Height in the Frame option decides the ratio of the frame in which the patterns appears in relation to the size of the display. Hence, seize of the pattern trajectory is limited by a Frame within the overall display, which is made invisible in the software program. This invisibility is necessary so the patient does not know when the target cursor on the screen has to change direction as it becomes close to the Frame.
9. The value in "Speed scaling" decides seize or scaling of the line graph and the bar graph in the top right box and the bottom left box, respectively. It is just used for visualization of how the speeds varies (line graph) and how much time is relatively spent in different speed sections (bar graph) of a generated pattern.
10. The horizontal blue line in the top right box in the line graph visualizes the threshold. The lines, above threshold, represent the straight parts (with faster speeds) and the lines, below threshold, represent the curves in the pattern trajectory (with slower speeds).
11. The horizontal red line and the horizontal green line in the top right box in the line graph visualizes the upper limits (straight parts) versus the lower limits (angles)
12. Add pattern requires number of segments and number of paths (patterns). With these values filled in, after one or more classes of movement patterns have been generated once, along with their predefined criteria according to the other mandatory fields marked an asterix values filled in, new patterns can always be added into the database for an existing movement class. A new movement pattern class can also be generated by filling in different criteria in the above-mentioned boxes.
13. Search button will list all patterns matching the "Path Selection" criteria. If no path selection criteria are entered, then all patterns in the databank will be listed.
14. Select Paths option currently allows one pattern to be chosen and recalculated
15. Recalculation allows a pre-selected existing pattern in the "Select Paths" list (14) to be updated. The recalculation button is activated after the desired alterations have been made in the one or more of the above-mentioned criteria in FIG. 1. The Recalculate button is therefore a way to edit and save an existing pattern in the database.
16. Patterns can be deleted using the delete button. The Delete button is activated only after selecting pattern from the "Select Path" list.
17. Patterns are of three types, implemented into one of three categories: Exercise, Measurement and Pre-Test.

Figure 3:
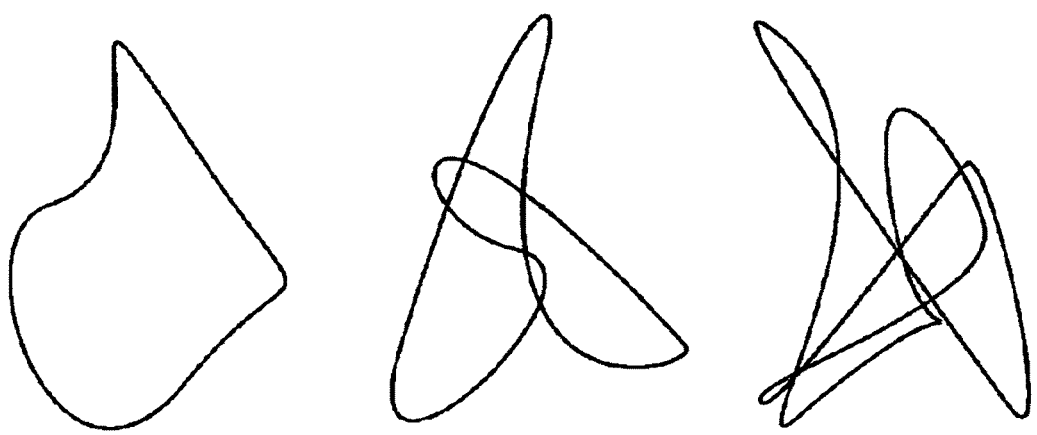
FIG. 3 shows examples of generated patterns in different difficulty classes

Value selected from user level decides pattern difficulty level; in one current embodiment three levels can be chosen: Easy, Medium or Difficult (FIG. 3).

The invention is not limited to the embodiments described above and shown and numbered in FIG. 1, which only have the purpose of illustrating and exemplifying. This patent application is intended to cover all adaptations and variants of the preferred embodiments described herein and consequently the present invention are defined by the wording of the accompanying claims and the equivalents thereof. Thus, the method may be modified in all feasible ways within the scope of the accompanying claims.

It should be pointed out that the creation of the curves in the said incremental difficult movement patterns may be generated by different approaches in computer graphics. The Bézier curve (see http://www.moshplant.com/direct-or/bezier/) is one way of creating the curves in computer graphics for the said method. Another method is the Natural Cubic spline method (http://mathworld.wolfram.com/CubicSpline.html), which is more precise in the mathematical field of numerical analysis and is therefore preferred for the said method. Thus, the creation of patterns may be modified in all feasible ways according to existing computer graphics approaches and computer graphics approaches developed in the future.

It should be pointed out that in other embodiments of the new method, different outcome measures from the ones presented in the presently exemplified embodiment can be implemented at a later stage. The same applies for the feedback, which can be implemented in numerous and various ways in alternative versions contemplated of the method of the invention.

It should be pointed out that all information concerning terms and parameters only indicate mutual relationship in the described embodiments, which relationship may be changed if the method according to the invention is provided with another design.

It should be pointed out that even if it is not explicitly mentioned that features from one specific embodiment can be combined with the features of another embodiment, this should be regarded evident when possible.

In yet a further embodiment of the invention, the method and system can be configured as an integrated part of a more comprehensive software and computer system, referred to herein as a "NeckCare Unit", which contains patient self-assessment, measurements and treatment (exercises) methods.

Figure 2:
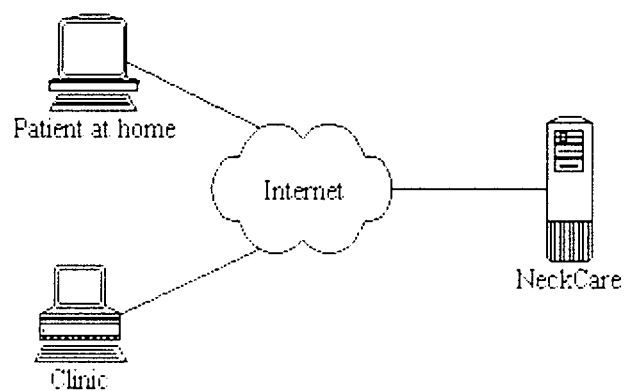
FIG. 2 illustrates how the novel assessment and treatment methods are made available for health care practitioners over the Internet through a server.

FIG. 2 shows how the novel assessment and treatment methods are made available for health care practitioners over the Internet through a server. There are three computer stations involved in this setup: 1. "NeckCare" station, which contains the Pattern Generation Program as described herein above and controls all internet connections with the clinics. 2. Clinician stations, which download assessment and treatment methods for patient's use in the clinics. 3. Patient stations, which download the treatment (exercise) part of the program from clinicians' desktops for patient's self-treatment at home or location of choice such as in an office.

Correct placement of sensor on patient's head is important to obtain standardized results. Also, since the data resides over the server—good speed Internet connectivity is mandatory in order to perform a test. If due to network latency or due to other network error—connection between Clinic and NeckCare station is lost, then the test has to be restarted upon restoration of connectivity.

The invention provides the benefits of being able with the combination of easy and more difficult patterns, to differentiate subjects with biologically genuine symptoms and subjects who try to fake results for personal gain, an issue of great concern for patients with neck pain after motor vehicle collisions and their insurance companies because of the medical-legal implications.

REFERENCES

1. Slinger R T, Horsley V. Upon the orientation of points in space by the muscular, arthrodial, and tactile senses of the upper limbs in normal individuals and in blind persons. Brain 1906; 29:1-27.
2. Revel M, Andre-Deshays C, Minguet M. Cervicocephalic kinesthetic sensibility in patients with cervical pain. Arch Phys Med Rehabil 1991; 72:288-91.
3. Heikkilä H, Åström PG Cervicocephalic kinesthetic sensibility in patients with whiplash injury. Scand J Rehabil Med 1996; 28: 133-138.
4. Rix G D, Bagust J. Cervicocephalic kinaesthetic sensibility in patients with chronic, nontraumatic cervical spine pain. Arch Phys Med Rehabil 2001; 82: 911-919.
5. Loudon J K, Ruhl M, Field E. Ability to reproduce head position after whiplash injury. Spine 1997; 22: 865-868.
6. Kristjansson E, Dall'Alba P, Jull G. Cervicocephalic kinaesthesia: reliability of a new test approach. Physiother Res Int 2001; 6: 224-235.
7. Kristjansson E, Hardardottir L, Ásmundardottir M, Gudmundsson K. A new clinical test for cervicocephalic kinesthetic sensibility: "The Fly" Arch Phys Med Rehabil 2004; 85: 490-495.
8. Shumway Cook A, Woolacott A. Motor control: Theory and Practical Application. Lippincott Williams & Wilkins, Philadelphia; 2001

The invention claimed is:

1. A method for assessing and grading sensorimotor impairment of a human subject which comprises
    a) generating in a computer a pattern which comprises a trajectory path,
    b) classifying said pattern in a class from a plurality of difficulty classes of patterns of incremental difficulty, wherein said difficulty classes are defined by parameters, including (a) number of curves in said trajectory path, (b) acuity of curves in said trajectory path, and (c) speed of the target cursor in curved parts of said trajectory path and in straight parts of said trajectory path,
    c) placing a movement sensor on the head or limb of said subject, which sensor is connected to said computer such that said computer can trace movements of said sensor, and output a tracing cursor on a display,
    d) drawing said classified generated trajectory path on said display with a target cursor after the subject has been instructed to follow the target cursor by moving the tracing cursor, such that acuity of curves in said trajectory path and speed of the target cursor are related as defined by a ⅔ Power Law,
    e) determining the correlation and/or deviation of said tracing cursor from said target cursor, wherein the correlation measurement comprises determining an amplitude accuracy, a directional accuracy, and a jerk index,
    f) determining a graded impairment assessment of sensorimotor function of said subject, based on the measured correlation and/or deviation in step e).

2. The method of claim 1, for assessing and further for training sensorimotor function of said human subject, wherein a pattern is generated in a selected difficulty class based on previous assessment of said subject by said method.

3. The method of claim 1, wherein said plurality of difficulty classes are defined by one or more of the following parameters:
    a) threshold defining where a curve in the pattern path starts,
    b) length of said trajectory path,
    c) ratio between curved versus straight parts of said trajectory path,
    d) speed and reaction time of the tracing cursor relative to the speed and temporal movement of the sensor, e) the speed of the target between two pixel points on the display device, f) the size and or part of a frame within the display device that the target is moving within on the display device.

4. The method of claim 3, wherein said pattern is generated in situ by a program which takes into account one or more of said parameters.

5. The method of claim 3, wherein said pattern is retrieved from a database of a plurality pre-generated patterns, which have been generated based on one or more of said parameters.

6. The method of claim 4, wherein the pattern is randomly generated or selected within the pre-selected difficulty class.

7. The method of claim 3, wherein said plurality of difficulty classes are defined by all of parameters a) to f).

8. The method of claim 1, wherein said pattern is a two-dimensional pattern.

9. The method of claim 1, wherein said pattern is a three-dimensional pattern and said display provides three-dimensional viewing, such as through stereo goggles.

10. The method of claim 1, for assessing sensorimotor function of a body part selected from the group consisting of head/neck area, arm and elbow, hand, foot.

11. The method of claim 1, wherein said pattern comprises a background which can move relative to the target cursor.

12. The method of claim 3, wherein said parameter can be adjusted so as to create a pattern is more in one quarter of the display than any of the other three quarters.

13. The method of claim 6, wherein said patterns can be created which are movement plane-specific such that target cursor moves more in one plane selected from the sagittal, frontal and transverse planes.

14. The method of claim 1, further comprising subjecting the subject to external perturbations selected from vibration stimuli for the superficial neck muscles and for the superficial muscles at remote body site, unstable sitting or standing surfaces, external weights applied to subject's body.

15. The method of any claim 1, wherein said assessment of sensorimotor function comprises an assessment on whether deviations of the tracing cursor from the target cursor are due to feigned or true effects on sensorimotor function.

16. A system for assessing and grading sensorimotor impairment and training sensorimotor function of a human subject, the system comprising:

a computer installed with a computer program, an output display connected to said computer, a motion tracking sensor connected to said computer, wherein the motion tracking sensor is configured to be placed on the head or limb of a human subject, wherein the sensor is connected to the computer such that the computer can trace movements of the sensor, and output a tracing cursor on said output display, wherein the system is further configured to draw a classified generated trajectory path on said output display with a target cursor after the subject has been instructed to follow the target cursor by moving the tracing cursor, said computer program when run on the computer generates a pattern comprising the trajectory path that is traced on said display with the target cursor, such that acuity of curves in said trajectory path and speed of the target cursor are related as defined by a ⅔ Power Law the program further outputs on the display a tracking cursor, which follows the motion of said motion sensor, the program calculates a correlation and/or deviation between said target cursor trajectory and the trajectory of the tracking sensor, and outputs data indicative of the sensorimotor impairment of the subject, wherein the correlation measurement comprises determining an amplitude accuracy, a directional accuracy, and a jerk index, the program capable of generating a plurality of difficulty classes of patterns of incremental difficulty, wherein said difficulty classes are defined by parameters, including (a) number of curves in said trajectory path, (b) acuity of curves in said trajectory path, and (c) speed of the target cursor in curved parts of said trajectory path and in straight parts of said trajectory path.

17. The system of claim 16, wherein said plurality of difficulty classes are defined by one or more of the following parameters:

a) threshold defining where a curve in the pattern path starts, b) length of the pattern path, c) ratio between curved versus straight parts of the pattern path, d) speed and reaction time of the tracing cursor relative to the speed and temporal movement of the sensor, e) the speed of the target between two pixel point on the display device f) the size and or part of a frame within the display device that the target is moving within on the display device.

18. The system of claim 16, wherein said pattern is a three-dimensional pattern and said display provides three-dimensional viewing, such as stereo goggles.

19. The system of claim 16, wherein said output display is remotely connected to said computer, such that said human subject with said motion tracking sensor and output display is in a first location and said computer in a second location.

20. The system of claim 16, comprising a second computer in a third location, through which a service provider can provide said human subject with controlled assessment and/or training at the first location.

21. The system of claim 16, wherein said pattern is generated by calculation for each operation or retrieved from a database of pre-generated patterns.

22. The system of claim 21, wherein the pattern is randomly generated or selected within the pre-selected difficulty class.

* * * * *